(12) United States Patent
Genova et al.

(10) Patent No.: US 6,581,590 B1
(45) Date of Patent: Jun. 24, 2003

(54) INHALATION ACTUATED DEVICE

(75) Inventors: Perry A. Genova, Chapel Hill, NC (US); Robert C. Williams, Raleigh, NC (US); Keith Wakefield, Clayton, NC (US)

(73) Assignee: IEP Pharmaceutical Devices Inc., Raleigh, NC (US)

( * ) Notice: Subject to any disclaimer, the term of this patent is extended or adjusted under 35 U.S.C. 154(b) by 0 days.

(21) Appl. No.: 09/531,732

(22) Filed: Mar. 21, 2000

(51) Int. Cl.[7] .............................................. A61M 11/00
(52) U.S. Cl. ............................. 128/200.23; 128/200.14; 128/203.12
(58) Field of Search ................... 128/200.14, 200.21, 128/20.23, 203.12

(56) References Cited

U.S. PATENT DOCUMENTS

| | | | |
|---|---|---|---|
| 3,001,524 A | * 9/1961 | Maison et al. | 128/200.23 |
| 3,320,952 A | * 5/1967 | Wright | 128/200.23 |
| 3,361,306 A | * 1/1968 | Grim | 128/200.23 |
| 3,456,646 A | * 7/1969 | Phillips et al. | 128/200.23 |
| 3,490,452 A | * 1/1970 | Greenfield | 128/200.23 |
| 4,291,688 A | * 9/1981 | Kistler | 128/200.23 |
| 4,648,393 A | 3/1987 | Landis et al. | |
| 4,664,107 A | 5/1987 | Wass | |
| 4,955,371 A | 9/1990 | Zamba et al. | |
| 5,027,808 A | 7/1991 | Rich et al. | |
| 5,057,281 A | 10/1991 | Torti et al. | |
| 5,060,643 A | * 10/1991 | Rich et al. | 128/200.23 |
| 5,069,204 A | 12/1991 | Smith et al. | |
| 5,119,806 A | 6/1992 | Palson et al. | |
| 5,184,761 A | * 2/1993 | Lee | 222/402.2 |
| 5,217,004 A | 6/1993 | Blasnik et al. | |
| 5,345,980 A | 9/1994 | Burt et al. | |
| 5,347,998 A | 9/1994 | Hodson et al. | |
| 5,349,944 A | * 9/1994 | Chippendale et al. | 128/200.14 |
| 5,388,572 A | 2/1995 | Mulhauser et al. | |
| 5,408,994 A | 4/1995 | Wass et al. | |
| 5,447,150 A | 9/1995 | Bacon | |
| 5,507,281 A | 4/1996 | Kuhnel et al. | |
| 5,655,516 A | 8/1997 | Goodman et al. | |
| 5,692,492 A | 12/1997 | Bruna et al. | |
| 5,775,320 A | 7/1998 | Patton et al. | |
| 5,809,997 A | 9/1998 | Wolf | |
| 5,819,726 A | 10/1998 | Rubsamen et al. | |
| 5,826,570 A | 10/1998 | Goodman et al. | |
| 5,826,571 A | 10/1998 | Casper et al. | |
| 5,904,139 A | 5/1999 | Hauser | |
| 6,029,662 A | 2/2000 | Marcon | |
| 6,116,234 A | * 9/2000 | Genova et al. | 128/200.23 |
| 6,142,339 A | * 11/2000 | Blacker et al. | 222/23 |
| 6,148,815 A | * 11/2000 | Wolf | 128/205.23 |
| 6,260,549 B1 | * 7/2001 | Sosiak | 128/200.23 |
| 6,318,361 B1 | * 11/2001 | Sosiak | 128/200.23 |
| 6,325,062 B1 | * 12/2001 | Sosiak | 128/203.25 |

* cited by examiner

Primary Examiner—Weilun Lo
Assistant Examiner—Joseph F. Weiss, Jr.
(74) Attorney, Agent, or Firm—Frommer Lawrence & Haug LLP; Ronald R. Santucci

(57) ABSTRACT

An inhalation activated device or dispenser is disclosed. In particular, the dispenser comprises a housing for containing an aerosol canister containing a medication wherein the canister is moveably contained in the housing upon inhalation by the patient whereby a metered dose of a spray is initiated and a controlled period of time is established by a dwell means.

18 Claims, 7 Drawing Sheets

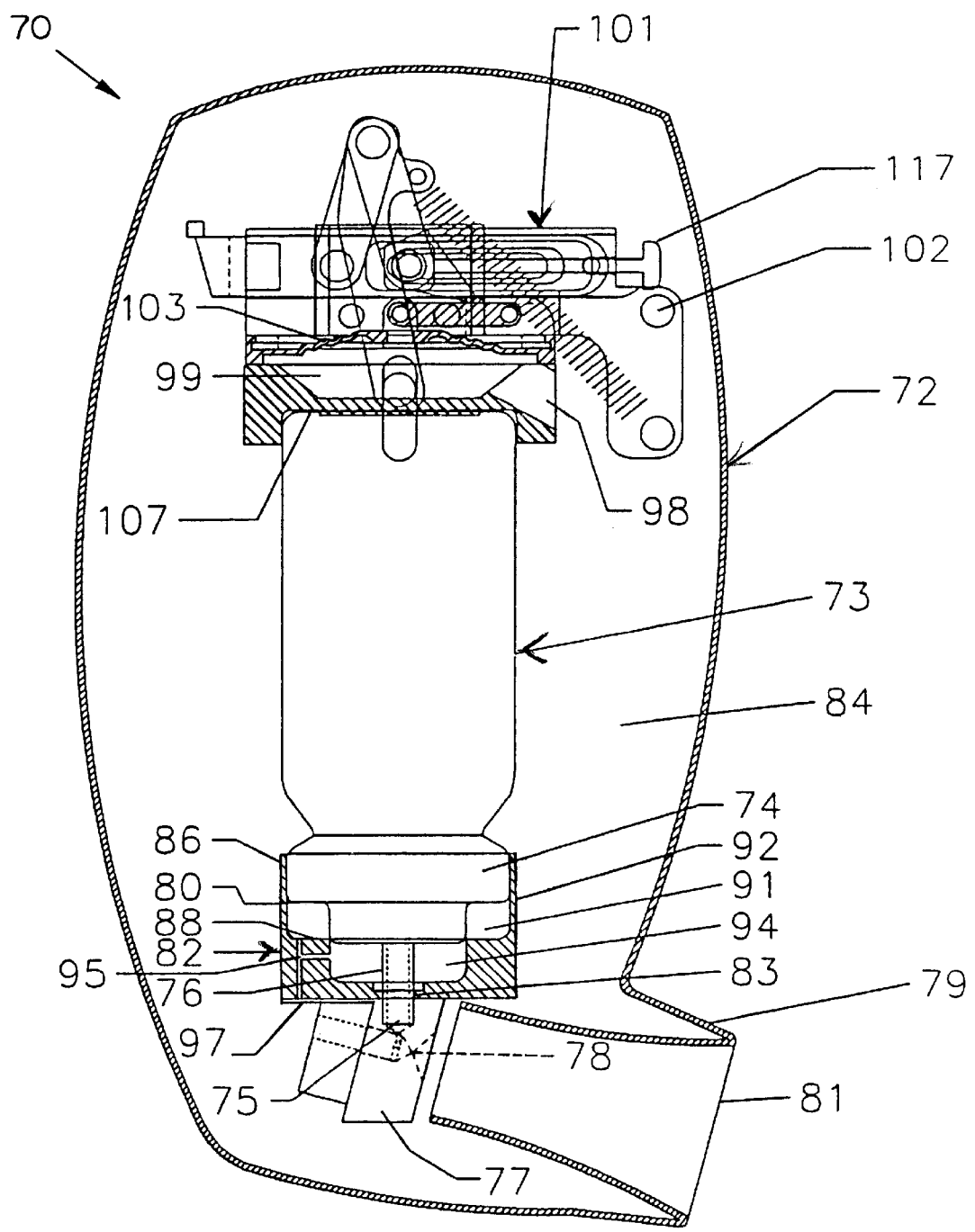
F I G. 1A

INHALATION ACTUATED DEVICE

BACKGROUND OF THE INVENTION

1. Field of the Invention

This invention relates to a breath-actuated device. In particular, the device is directed to what is typically referred to as an inhaler having an aerosol medication containing canister, which upon actuation releases a metered dose of medication to a patient.

2. Description of the Prior Art

There are a variety of inhalation devices which release aerosol medication, in a continuous spray or in a metered dose or predetermined amount of medication, directly into the patient's mouth, nasal area or respiratory airways. Typically, these devices are actuated by the pressured actuation of the user's fingers, button action, or other related manual techniques. Although some are activated by the inhaling action of the users, heretofore there are few simple, inexpensive and reliable breath actuated devices developed.

Metered dose aerosol canisters of the medicine to be inhaled into the mouth, nasal areas or respiratory airways are manufactured by a variety of pharmaceutical companies. Metered dose aerosols are much the same as non-metered aerosol except that when the valve is depressed, a continuous spray does not result but instead a predetermined measured spray releases delivering a fixed amount of medication. Examples of such metered dose inhalers are set forth in U.S. Pat. No. 5,544,647, issued Aug. 13, 1996 entitled "Metered Dose Inhaler"; and 5,622,163 issued Apr. 22, 1997 entitled "Counter for Fluid Dispensers"; and U.S. patent application Ser. No. 09/241,010 filed Feb. 1, 1999 entitled "Metered Dose Inhaler Agitator" (commonly assigned), the disclosures of which are incorporated herein by reference. Devices of this type have proven to be very satisfactory, however, as with everything else, improved operation is desirable.

Aerosols used with manually actuated inhaler devices often incorporate ambient air with the volume of medication permitting a complete breath of air by the patient while inhaling the medication. Alternatively, aerosol medicines are also available in continuous spray, which continually spray as long as the valve or nozzle pin is depressed.

Proper use of these manual actuated devices requires that the spray be activated at the beginning of the inspiratory cycle, so that the medication is carried into the lungs rather than being deposited in the mouth or throat. If this actuation is not correctly coordinated with the inspiratory phase the metered dose may be deposited differently with each actuation and potentially compromise the therapeutics and safety of the product. A breath actuated device helps eliminate this problem by making the product easier to coordinate and more patient friendly, with predictable delivery and dispersion in the respiratory airways.

There are numerous factors leading to poor coordination ranging from the user's inherent skills, associated with the geriatrics and pediatrics to patients with impaired physical facilities. Recognizing the need for correct and accurately delivered doses in the asthmatics, COPD patients and, as with other patients with other respiratory illnesses, a reliable breath activated device would improve the quality of life for these respiratory ill patients.

SUMMARY OF THE INVENTION

The present invention comprises a metered dose dispenser for aerosol medication contained in a housing having a mouthpiece for insertion into a patient's mouth. A mechanical actuator mechanism is provided in cooperation with the canister, in its initial locked position, which upon inhalation by a patient causes the canister to dispense a metered dose of medication as a spray from the mouthpiece to the patient. The dose is established by a metering valve associated with the canister. A dwell means is provided which ensures complete discharge of the metered dose and subsequently, complete filling of the metering valve with the next dose after the dispensing.

BRIEF DESCRIPTION OF THE DRAWINGS

FIG. 1A is a partial side cross-sectional view of the metered dose inhaler in its locked or cocked state prior to inhalation;

DETAILED DESCRIPTION OF THE PREFERRED EMBODIMENT

Figure 1B:
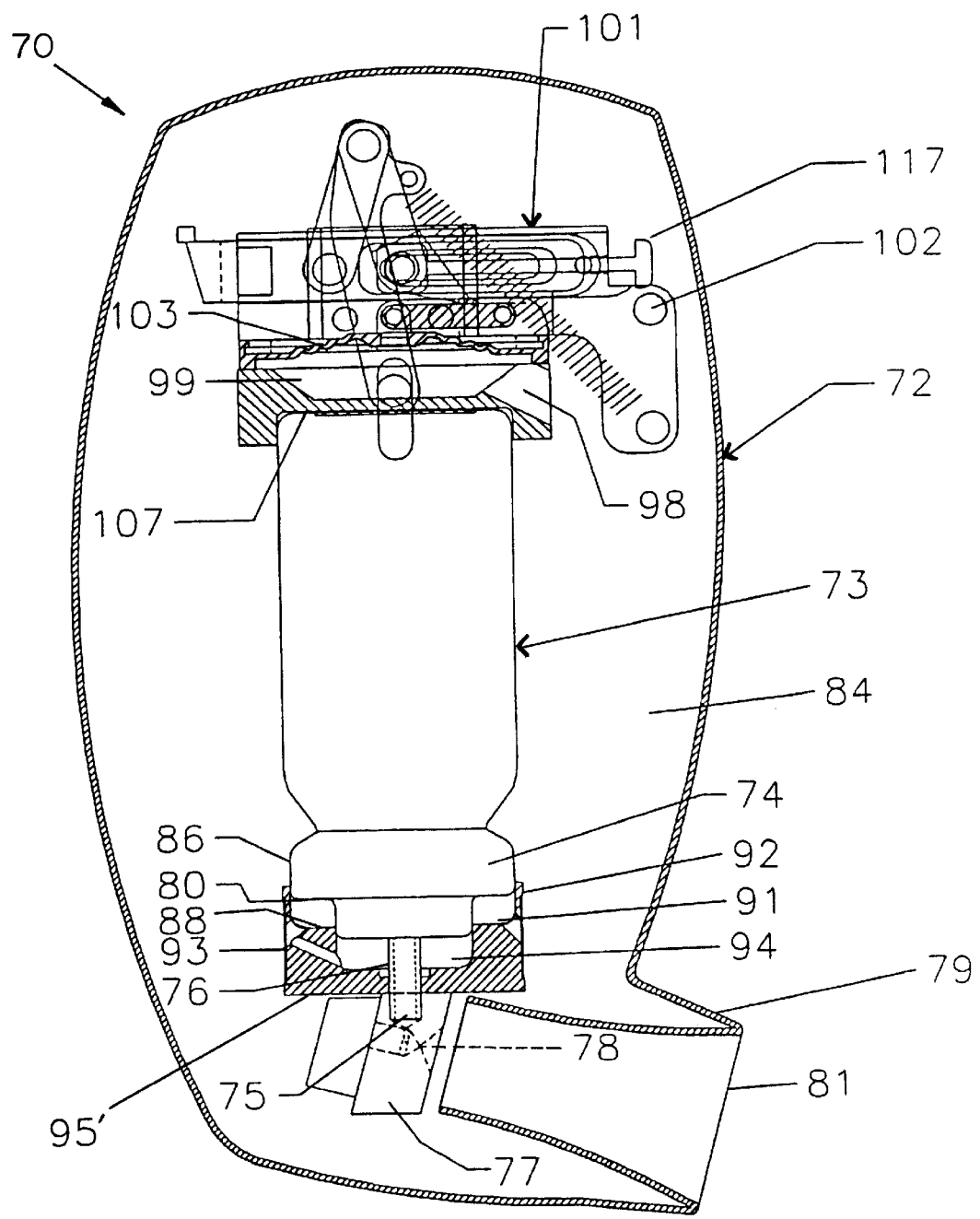
FIG. 1B is a partial side sectional view of an alternative embodiment of the inhaler shown in FIG. 1A.

Referring now more particularly to the Figures, there is shown a breath activated device or metered dose inhaler, sometimes referred to as the dispenser, generally designated by the reference numeral 70.

The dispenser 70 includes a housing 72 for containing an aerosol container or canister 73, containing a medication, e.g. beclomethasone dipropionate, cortisone, epinephrine, erythromycin, etc., or a placebo and liquid propellant, e.g. 1,1,1,2-tetrafluoroethane (HFC-134a), 1,1,1,2,3,3,3-heptafluoropropane (HFC-227), or other propellant suitable for purpose. The housing 72 may be fabricated from a metal, e.g. aluminum, etc., or a plastic, e.g. ABS, polypropylene, polyethylene, etc. or other material suitable for purpose. Where a disposable inhalation device 70 is contemplated, the housing 72 is preferably molded of a plastic material. The canister 73 is a conventional pressurized container, and may also be fabricated from a metal, such as, aluminum, etc., or plastic, e.g. ABS, polypropylene, etc., or other material. If the dispenser 70 is intended to be disposable, plastic material is preferred.

The canister 73 has at one end a metering dispensing valve 74 for dispensing a dose of medication from the canister 73 through a hollow valve stem 76, to a nozzle 77 which has an exit opening 78 at its far end which communicates (optionally) with a conventional spacer (not shown). The valve stem 76 is normally "charged" in its extended position (FIG. 1A) but when depressed (FIG. 1D) will discharge to dispense an aerosol stream of medication from the canister 73 via valve 76. In this regard, the valve 74 has an internal spring (not shown) which biases the stem 76 so that it is extended before discharging of the device 70 and which returns to its original position after discharging.

The nozzle 77, typically fabricated from polyethylene, polypropylene, etc., is centrally located in alignment with the aperture or opening 75 of the valve stem 76 where upon depression of the stem 76 a metered quantity or dose of the medication is dispensed from the container 73 through the valve 74.

In operation, the medication is dispensed from the canister 73 through the valve 74 through the stem 76 into the nozzle 77 through its exit 78 into a mouthpiece 79. The mouthpiece may be integrally formed in or separately attached to the end of the housing 72. The mouthpiece 79 has an opening 81 which is placed into a patient's mouth (not shown) for treatment with the medication. The dispensed dose of medication passes through the nozzle 77, optionally into a spacer (not shown), into the mouthpiece 79 and out the opening 81 into the patient's mouth and lungs.

Any conventional nozzle 77 can be employed depending upon the aerosol spray desired. A particular nozzle may be selected by the skilled artisan to produce a particular shape or plume, including the acceleration of the medication aerosol spray.

Preferably the vortex nozzle described in U.S. application Ser. No. 60/135,056, filed on May 20, 1999, incorporated hereinto by reference in its entirety, may be employed. Also, the metered dose counting features as set forth in the aforenoted patents and applications may also be included in the present invention as would be readily apparent to those skilled in the art.

The housing 72 comprises a chamber 84 into which the canister 73 is inserted with its stem 76 down. The housing 72 includes a dwell chamber body 82 which may be fabricated from LDPE, polypropylene or other material suitable for purpose. The dwell chamber body 82 receives the container 73 with the valve 74 and the stem 76 in communication with an aperture orifice 83. The orifice 83 serves to direct the medication travelling from the stem 76 through the nozzle 77 and its exit 78, optionally through the spacer (not shown), and to the mouthpiece opening 81.

Referring to FIG. 1A, the dwell chamber body 82 is contoured to slideably fit and hold the valve 74, the stem 76 and includes an upper circumferential lip 86. The dispenser 70 is armed or cocked by a handle (not shown). This arms the actuator mechanism or means 90 (see FIG. 3), the stem 76 is thereby depressed whereby the metered dose from the valve is dispensed or released. The dwell chamber body 82, in association with the actuator mechanism 90, serve to keep the container 73, valve 74 and stem 76 in a depressed position for a desired period of time, e.g. about 10 milliseconds to about 4 seconds. This ensures adequate time for the metering valve to release the medication. When the valve stem 76 returns to its extended position the metering valve is charged with another dose and is then ready for the next use.

In its dwelled position (FIG. 1D), the dwell chamber body 82 engages the surface 80 of the canister 73 a distance from annular surface 88 of the dwell chamber body 82 to form an upper dwell chamber 91 having a first dimension and a lower dwell chamber 94 as well having a smaller second dimension.

Figure 1C:
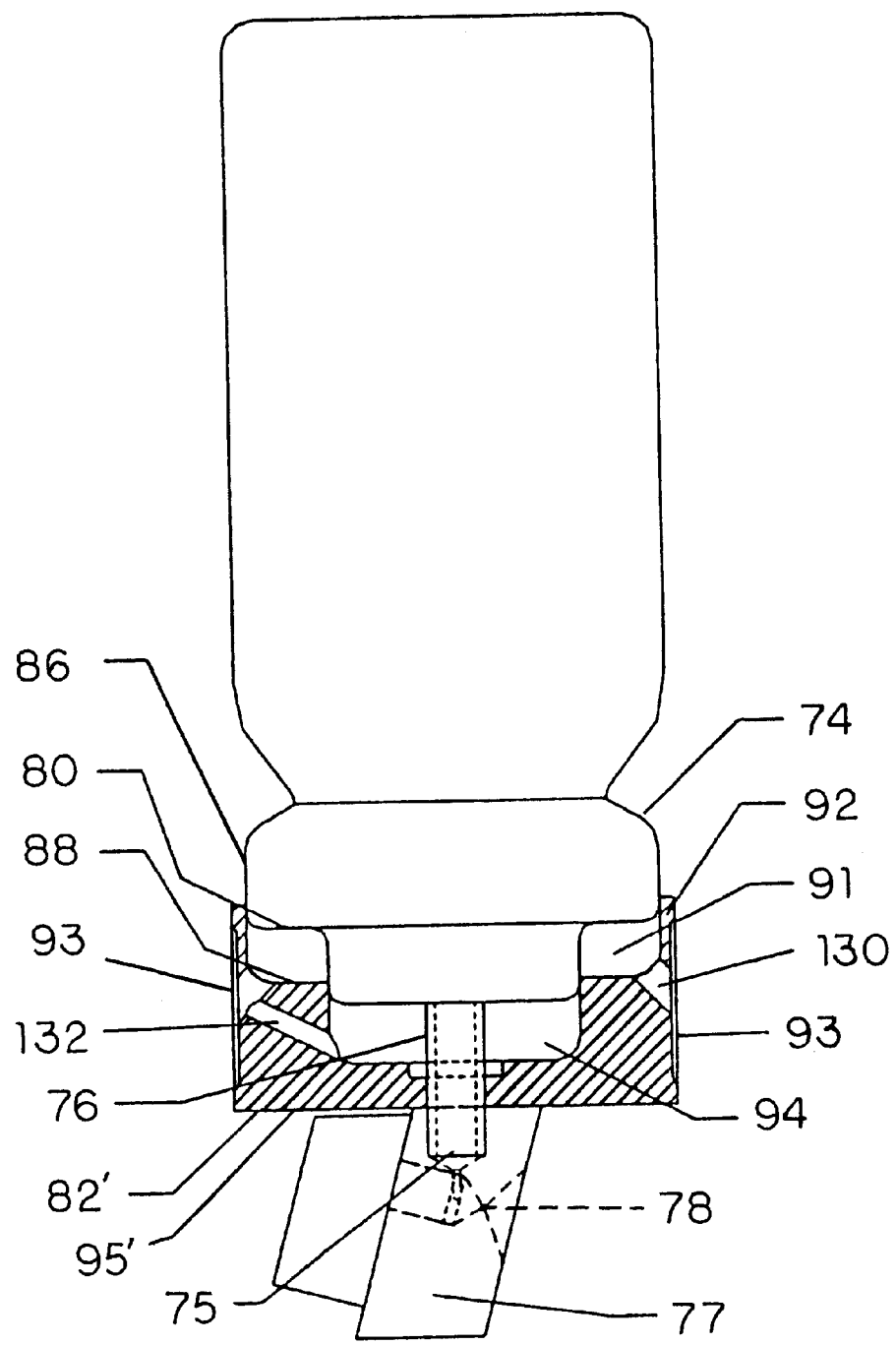
FIG. 1C is a somewhat enlarged partial side sectional view of the medication canister and dwell chamber of embodiment 1B in its up (not dwelled) position.
Figure 1D:
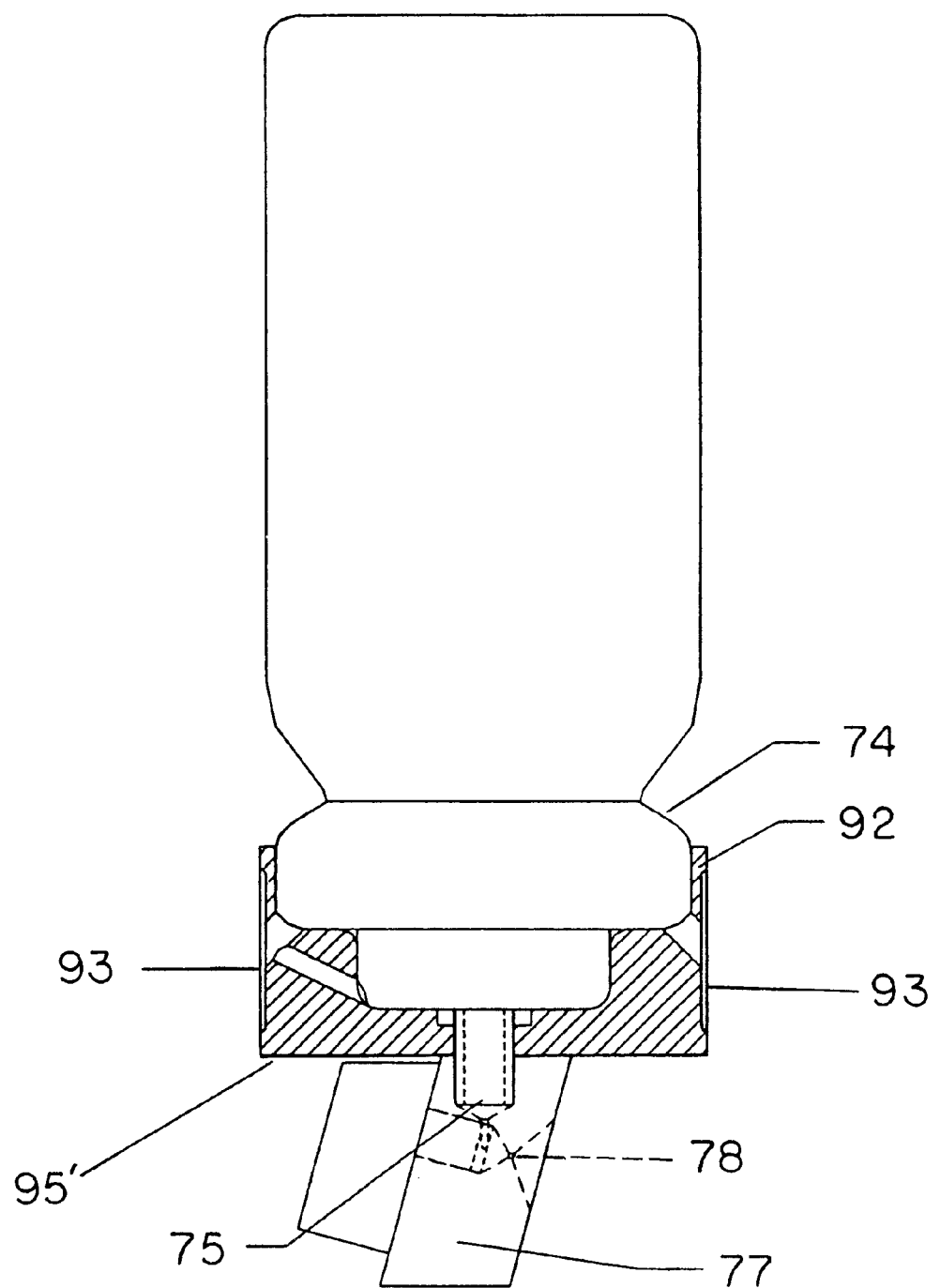
FIG. 1D is a somewhat enlarged partial side sectional view of the medication canister and dwell chamber of embodiment 1B in its down (dwelled) position.

The actuator mechanism 90 (FIG. 2), causes the movement of the canister 73 from a first or not dwelled position as shown in FIGS. 1A–1C to a second or dwelled position shown in FIG. 1D. In the dwelled position, the canister 73 bottoms out in the lower dwell chamber 94 causing the medication to be discharged during inhalation by the patient. To prevent any escape of the medication upwardly out of the dwell chamber body 82, and to accomodate variation in size of stems 76, the dispenser 70 may include a soft seal gasket (not shown) located in the dwell chamber body 82.

The upper dwell chamber 91 and the lower dwell chamber 94 in the undwelled position contain air which is allowed to escape upon depressing the canister 73, via T-shaped vent 95. Through the engagement of the valve surfaces 74 with the dwell chambers 91 and 94, there is a sliding relationship which however retards the return of the canister 73 to the undwelled position due to the engagement therebetween when the canister is depressed. This is the result of a vacuum formed in the chambers when the air is forced out. The vent 95 between the first dwell chamber 91 and the second dwell chamber 94 extend to the outside of dwell chamber body 82 to expel the air upon activation of the dispenser 70. Additionally, the walls 92 of the upper chamber 91 are of thin cross section which may expand and allow a certain amount of air to escape through annular space 126. An elastomeric flap or one way check valve 97, typically fabricated from silicone, etc. permits air passing through the vents 95 and out of the dwell chamber body 82.

In addition, the first dwell chamber 91 acts as a sort of dash pot to cushion or dampen the movement of the canister 73 and its elements to avoid shock thereto by the activation by means 90.

Turning now briefly to the embodiment shown in FIGS. 1B–1D, this is the same as that shown in FIGS. 1A, 2–4, with the exception of the dwell chamber body 82' (corresponding but differently constructed parts being designated with a prime). In this embodiment there is provided a venting mechanism 95' comprising a series of radial vent tubes 130 for venting dwell chamber 91 and a tubular vent 132 for venting dwell chamber 94. Positioned about the outside of the dwell chamber body 82' is an elastomeric sleeve valve 93. This sleeve valve 93 acts as a one way check valve and is sufficiently flexible so as to expand outward and permits air to pass through to escape from chambers 91 and 94 when the canister 73 is being pushed down into the dwell position. Subsequent to this, sleeve valve 93 returns to its original position sealing off the vents thereby causing a vacuum resistance which prevents the canister from returning to its rest position thereby maintaining the dwell period.

Figure 2:
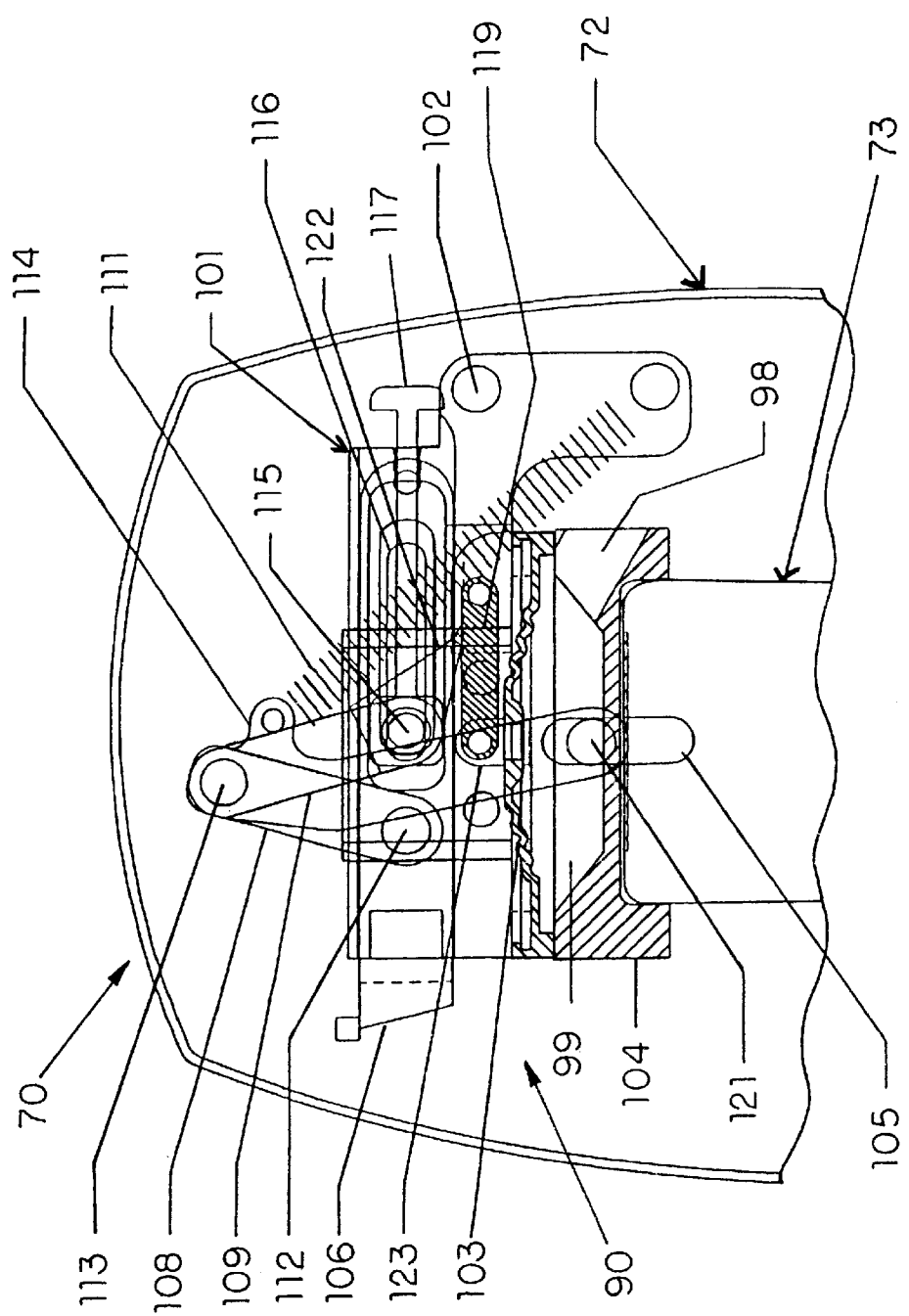
FIG. 2 is the partial cross-sectional view of the actuator mechanism of the dispenser of FIG. 1A–1D.

Turning now more particularly to the actuator mechanism 90, formed within the housing 72 is a suction tube 98 which communicates the mouthpiece 79 with a diaphragm chamber 99 of the actuator mechanism 90 (FIG. 2). The tube 98 provides air to the user of the dispenser 70 when the dispenser 70 is in position to be activated by the actuator mechanism 90. The actuator mechanism 90 comprises an actuator housing 101 which is pivotably affixed to the top of the housing 72 by means of a pivot pin 102.

Formed within the actuator housing 101 is the diaphragm chamber 99 having the suction tube 98 communicating therewith from the mouthpiece 79. The upper surface of chamber 99 is defined by means of an elastomeric diaphragm 103 whereas the lower surface of the chamber 99 is defined by a canister actuator 104 which serves to move the canister 73 to the dwell position upon the inhalation of the person using the dispenser 70. The diaphragm 103 is movably affixed within housing 101 contiguous to a second latch means 106. The actuator 104 is vertically moveable within housing 101 within a slotted member guide 105. The actuator upon activation moves vertically down the housing 72 guided by means of the slotted guide member 105 to sequentially (a) contact and move the canister 73 into the dwell position; (b) dispense the medication from the valve 74; (c) reload the valve 74 with the next dose of medication; and (d) return the dispenser 70 to its undwell position awaiting activation by another inhalation.

The second latch means 106, upon cocking of the dispenser 70 by the handle (not shown), latches the actuator housing 101 until the device 70 is activated by inhalation of the patient being treated. The canister actuator 104 additionally overlays the bottom surface 107 of the inverted canister 73.

Figure 4:
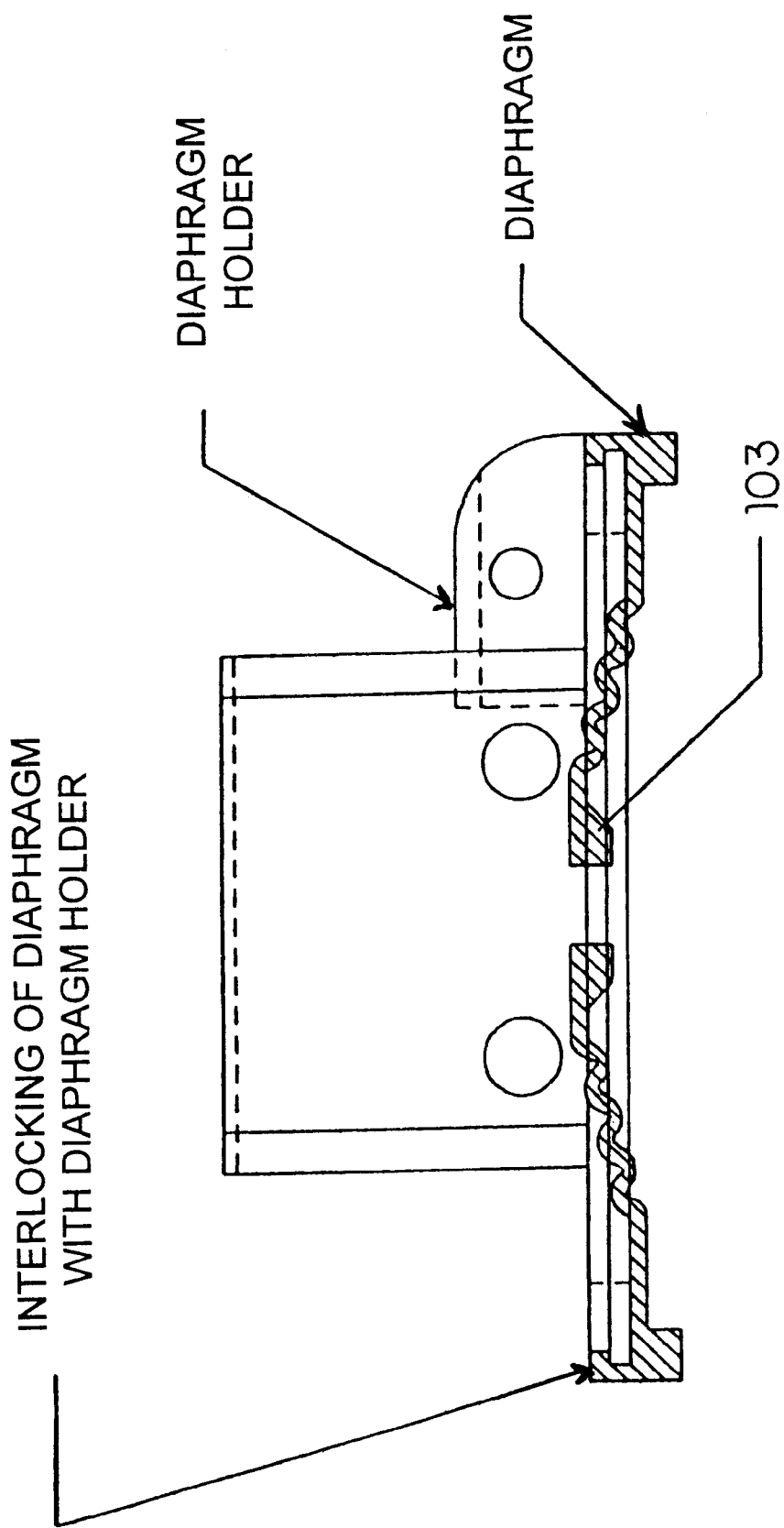
FIG. 4 is a partial cross-sectional view of the actuator mechanism of FIG. 2.

The diaphragm 103 is an elastic member, typically of circular configuration. The diaphragm 103 preferably has an elasticity suitable for permitting deformation in the presence of an inhalation through the suction tube 98. The diaphragm 103 is typically fabricated from a silicone rubber, neoprene, buna rubber, etc. and is of thin cross sectional area. Diaphragm 103 is molded with an internal feature designed to engage a lip on actuator housing 101 as shown in FIG. 4.

As indicated, referring to FIGS. 1A and 2, when a patient employs the dispenser 70 and inhales through the mouthpiece 79 and thus through suction tube 98, a negative pressure is created beneath diaphragm 103 in chamber 99. As a result, the diaphragm 103 is then displaced towards surface 107 of the canister 73 due to this negative pressure resulting in the movement of the actuator means 104 downward against the canister 73 and the ultimate dispensing of the medication.

The actuator housing 101, diaphragm 103 and chamber 99 may be fabricated from any material suitable for purpose. Note the dimensions and characteristics of the diaphragm 103 may be adjusted or modified (e.g. thickness, flexibility, or type of material) to allow for more or less suction to activate the device. The housing 101 has affixed to it by any conventional means the handle (not shown) which is vertically oriented. Upon depressing the handle (not shown), the housing 101 is locked in place by the second latch means 106 and the actuator mechanism 90 is in the armed position where an actuation or activation linkage arrangement of the actuator mechanism 90 is ready. Referring to FIG. 2, the actuation linkage arrangement comprises a drive arm 108 and a first latch means 109. The drive arm 108 and the latch 109 form a two link linkage system which is destined to be acted upon by a spring 111 via the drive arm 108. The bottom of the drive arm 108 is pivotably attached to the actuator housing 101 by means of a pivot pin 112. The top of the drive arm 108 is pivotably connected or attached to the top of the latch means 109 by means of a pivot pin 113. The bottom of the latch means 109 is pivotably connected to the housing 101 by means of a pivot pin 115 and is capable of moving horizontally within a slot 116 of housing 101 upon actuation of the dispenser 70.

A drive member 114 is pivotably attached at its top portion to the drive arm 108 by means of the pivot pin 113 and its bottom portion is pivotably attached to the canister actuator 104 by means of a pivot pin 121. When the dispenser 70 is fired by the actuator means 90, the drive arm 108 has a rotational force about pin 112 applied to it by the spring 111 whereby a translational force is applied by the drive member 114 to the canister actuator 104 driving it within the slot of the slotted guide member 105 against the canister 73.

Figure 3:
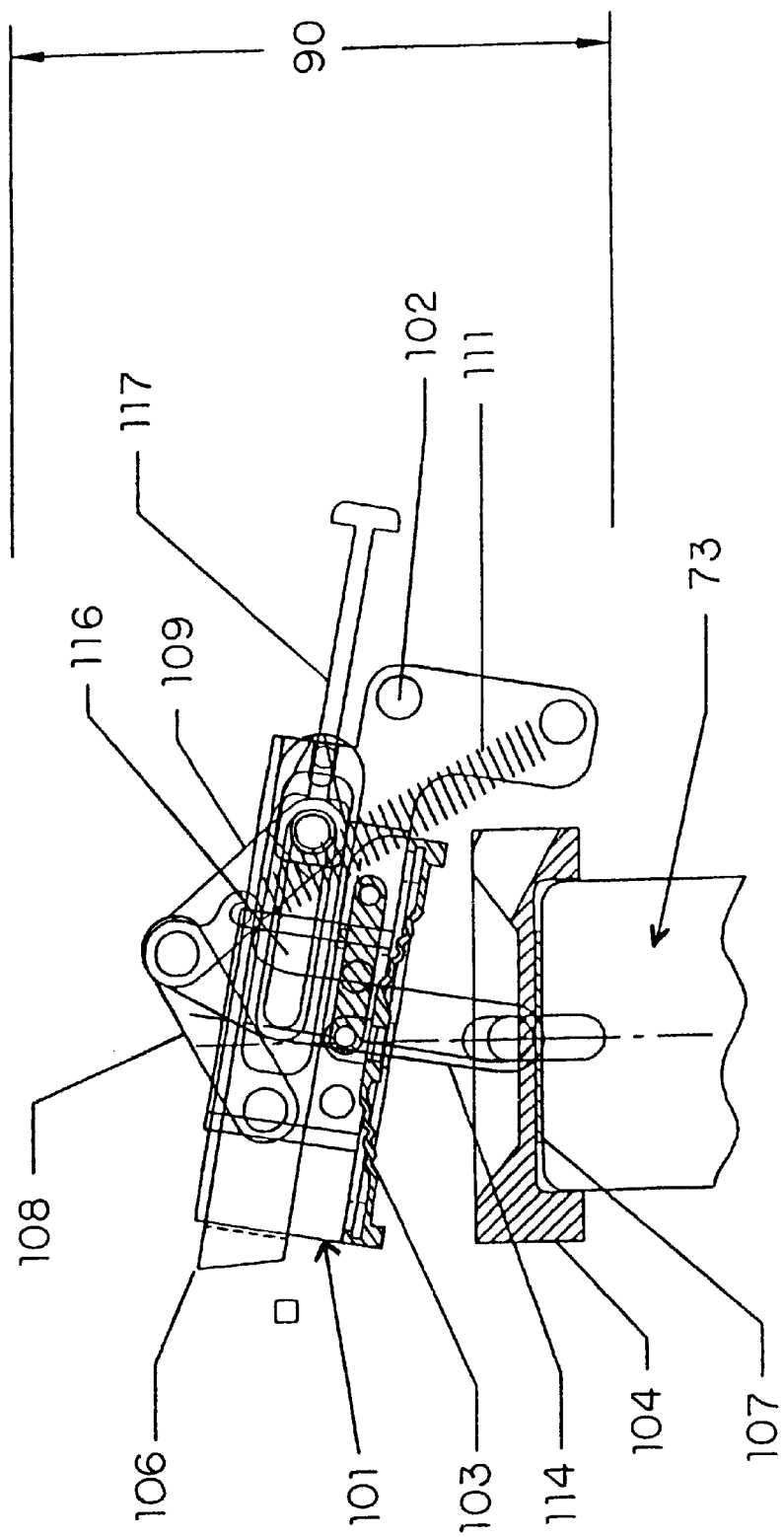
FIG. 3 is a partial cross-sectional view of the mechanism of FIG. 2 upon activation caused by inhalation.

As illustrated in FIG. 3, upon actuation of the dispenser 70 the canister actuator 104 slides away from the remainder of the diaphragm chamber 99, to permit air to enter into the device 70. In this regard, also as illustrated in FIG. 3, the housing 101 which is pivotably attached to the housing 72 by pin 102, upon activation of the dispenser 70, is released from the second latch means 106 and pivots up and away from the moving canister actuator 104 to also thereby permit air to enter into the fired device 70 after the canister 73 and valve 74 bottoms out. As previously indicated, the actuator 104 is in an adjacent or contiguous relationship with surface 107 of the canister 73 and forms with the bottom surface of chamber 99 prior to the activation of the dispenser 70.

Referring to FIG. 1A, the canister actuator 104, upon activation of the dispenser 70 by mechanism 90, is destined to contact the bottom surface 107 of the canister 73 and move the canister 73 and the valve 74 into and through dwell chamber 91 and into chamber 94 where the stem 76 is fully inserted into the nozzle 77. The stem 76 bottoms out to dispense the dose of medication through the valve.

When the device 70 is armed or cocked by means of the handle (not shown), a portion 122 of the first latch means 109 is prevented from moving by a keeper 119 which is pivotally attached by means of a pivot pin 121 to a diaphragm linkage 123 which is affixed, typically at the center, to the diaphragm 103 and is used to release the first latch means 109 upon movement of the diaphragm 103 which occurs upon inhalation by the patient being treated. The keeper 119, the diaphragm linkage 123 and the fixed diaphragm 103 all prevent portion 122 of the first latch means 109 from moving when the dispenser 70 is cocked or armed; which arming is accomplished by pressing the movable handle (not shown).

When the handle is pressed, it engages arming member 117 which pushes, via pin 115, portion 122 of the first latch means 109 towards the drive pivot point at pin 115. Then the two linkage system (drive arm 108 linked to the first latch means 109) folds around the common pivot point at the second pivot pin 113 until portion 122 of the latch 109 and the keeper 119 lock together. The second latching means 106 is engaged upon arming with the handle. The moveable handle (not shown) is then free to return to an extended position where further manipulation of the handle will not cause any action.

Referring to FIGS. 1A and 3, in use, the dispenser 70, armed by movement of the handle (not shown) and held in an upright position, a patient inhales through opening 81 of the mouthpiece 79. The inhalation creates a negative pressure along a flow path from the opening 81, through the suction tube 98 into the diaphragm chamber 99. The diaphragm 103 is acted upon by the negative pressure whereby it is deflected towards the canister 73 pulling on the keeper 119 via the diaphragm linkage 123 thereby moving the bottom portion 122 of the first latch means 109 along the slot 116 of the guide member 117 to release portion 122 of the latch means 109 from the keeper 119. This pulling action, which is vertical from the first latch means 109, allows latch linkage horizontal movement which translates perpendicularly to the movement of the diaphragm 103. This translation is caused by the spring 111 acting on the drive arm 108. The spring 111 urges the drive arm 108 to rotate about its pivot point at pivot pin 112 within the actuator housing 101 whereby portion 122 of the first latch means 109 slides along slot 116.

The rotation of the drive arm 108 translates to a linear, downward moving force to the drive member 114 driving the member 114 towards the canister 73 by means of the pin 121 along the slot of slotted guide member 105 contained therein to move the canister actuator 104 into contact with the surface 107 of the canister 73 and drive the canister 73 and its elements 74 and 76 into chambers 91 and 94 to deliver a metered dose to the patient.

When the canister 73 reaches the bottom of the lower dwell chamber 94, the stem 76 bottoms out and is completely compressed. At this juncture, the canister 73 is held in place by both vacuum and friction for a desired period of time which dictates that the aerosol dose of the medication is fully delivered to the patient and that the valve 74 is fully re-filled or replenished with the requisite dose of the medication, e.g. typically about 10 milliseconds to about 4 seconds. The internal valve spring (not shown) in the valve 74 of the canister 73 will slowly overcome the vacuum and friction forces after the requisite dwell time, e.g., 100 milliseconds, and return the valve stem 76, the valve 74 and the canister 70 to their original position.

It should be noted that variations to the actuator means 90 are envisioned. For example, spring 111 can be positioned beneath diaphragm 103 to provide an axial transitional force downward on canister actuator 104 upon the triggering of the device. Appropriate adjustment of the linkage arrangement can be made to accommodate the position of the spring in this regard. Other variations should be apparent to those skilled in the art.

Thus by the present invention its objects and advantages are realized and although preferred embodiments have been disclosed and described in detail herein, its scope should not be limited thereby rather its scope should be determined by that of the appended claims.

What is claimed is:

1. An inhalation activated dispenser, which comprises:
   (a) a housing means for receiving a canister containing an aerosol medication for dispensing a dose thereof to a patient which is moveable in said housing which movement causes a dispensing of medication from a dispensing means which requires a dwell time to refill to allow for dispensing a subsequent dose of medication;
   (b) inhalation means so as to allow for inhalation by a patient of medication;
   (c) an activation means for acting upon a canister upon the inhalation by a patient through said inhalation means causing movement from a first position to a second position whereupon a dose of medication is released therefrom; and
   (d) a dwell means within said housing means for maintaining a canister for a sufficient period of time in the second position to replenish a dose of said medication in a dispensing means contained therein.

2. The dispenser of claim 1, which further comprises a means for removing air from the dwell means prior to said release of dose.

3. The dispenser of claim 1, wherein said dwell means includes a first dwell chamber engageable with a canister for maintaining the canister for a dwell time.

4. The dispenser of claim 3, wherein said dwell means further comprises a second dwell chamber.

5. The dispenser of claim 4, which includes means for venting said first and second chambers.

6. The dispenser of claim 5, wherein said venting means includes a one way check valve.

7. The dispenser of claim 5, wherein said venting means includes an elastomeric sleeve valve.

8. An inhalation activatable dispenser for use with an aerosol container having a valve for dispensing aerosol from an outlet in the container, the valve having a hollow stem which is moveable relative to the container between an extended closed position and a compressed discharge position of the valve upon the inhalation of a patient, which comprises:
   (a) a housing, having a mouthpiece and an air passage therethrough terminating at said mouthpiece, for receiving and moveably retaining the aerosol container;
   (b) a nozzle seat within said housing with a means to receive the stem and a orifice communicating between the stem and said air passage;
   (c) an activator means for activating the dispense to dispense said metered dose comprising a latch means moveable between an engaged position in which it maintains the container in a first position and a release position which moves said container towards said nozzle to a second position to effect a release of a dose of medication whereupon upon the inhalation of the patient through said mouthpiece causes said container to move from the first position to the second position releasing a dose of medication;
   (d) a dwell means for establishing a dwell time period in which the container is in the second position so as to allow a refilling of a dose of medication for subsequent discharge.

9. The dispenser as defined in claim 8, wherein said activator means comprises,
   a container actuator, which is located at a bottom of a chamber, which is connected to said mouthpiece by said inhalation means, said actuator being in contact with the container and, moves the container toward said nozzle seat when said latch means is in said release position; and
   a diaphragm, which is located at a top of said chamber, which is pivotably affixed to a linkage means which cooperates with said latch means, wherein said diaphragm upon the inhalation by the patient moves said latch means into its release position to cause said container actuator to move the container toward said nozzle seat.

10. The dispenser as defined in claim 9, wherein said linkage means comprises,
    a latch cooperating with a keeper which is pivotably attached to said housing and which engages said latch, said keeper being pivotably attached to said diaphragm for movement with said diaphragm to cause release of said latch from said keeper.

11. The dispenser as defined in claim 10 which further comprises a drive member pivotably attached to and moveably by said linkage means for urging a force to said container actuator to move the container.

12. The dispenser as defined in claim 11 which further comprises a drive arm pivotably attached to said drive member where said drive arm urges said force to said drive member.

13. The dispenser of claim 8, which further comprises a means for removing air from said dwell means prior to releasing said dose.

14. The dispenser of claim 13, wherein said dwell means includes a first dwell chamber engageable with the canister for maintaining the canister for said dwell.

15. The dispenser of claim 14, wherein said dwell means further comprises a second dwell chamber.

16. The dispenser of claim 15, which includes means for venting said first and second chambers.

17. The dispenser of claim 16, wherein said venting means includes a one way check valve.

18. The dispenser of claim 16, wherein said venting means includes an elastomeric sleeve valve.

* * * * *

UNITED STATES PATENT AND TRADEMARK OFFICE
CERTIFICATE OF CORRECTION

PATENT NO. : 6,581,590 B1
DATED : June 24, 2003
INVENTOR(S) : Genova et al.

It is certified that error appears in the above-identified patent and that said Letters Patent is hereby corrected as shown below:

Column 7,
Line 43, cancel "a dispensing means contained therein" and replace it with -- said dispensing means, said dwell means causing a partial vacuum between the dwell means and the canister so as to retard movement of said canistser from said second position back to said first position for a predetermined period of time, said dwell means thereby establishing said dwell time --.

Column 8,
Line 18, add the following directly to the end of that line -- , said dwell means causing a partial vacuum between the dwell means and the canister so as to retard movement of said canister from said second position back to said first position for a predetermined period of time --

Signed and Sealed this

Twenty-first Day of June, 2005

JON W. DUDAS
*Director of the United States Patent and Trademark Office*